US010335105B2

United States Patent
Zhou (10) Patent No.: US 10,335,105 B2
(45) Date of Patent: Jul. 2, 2019

(54) METHOD AND SYSTEM FOR SYNTHESIZING VIRTUAL HIGH DOSE OR HIGH KV COMPUTED TOMOGRAPHY IMAGES FROM LOW DOSE OR LOW KV COMPUTED TOMOGRAPHY IMAGES

(71) Applicant: Siemens Healthcare GmbH, Erlangen (DE)

(72) Inventor: Shaohua Kevin Zhou, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/553,744

(22) PCT Filed: Apr. 28, 2015

(86) PCT No.: PCT/US2015/027875
§ 371 (c)(1),
(2) Date: Aug. 25, 2017

(87) PCT Pub. No.: WO2016/175755
PCT Pub. Date: Nov. 3, 2016

(65) Prior Publication Data
US 2018/0042564 A1    Feb. 15, 2018

(51) Int. Cl.
*A61B 6/00*    (2006.01)
*G06T 5/50*    (2006.01)
(Continued)

(52) U.S. Cl.
CPC .......... *A61B 6/482* (2013.01); *A61B 6/03* (2013.01); *A61B 6/5235* (2013.01); *G06T 5/50* (2013.01);
(Continued)

(58) Field of Classification Search
CPC . G06T 2207/20072; G06T 2207/20084; G06T 2207/30024; G06T 2207/30028;
(Continued)

(56) References Cited

U.S. PATENT DOCUMENTS

| | | |
|---|---|---|
| 8,467,570 B2 * | 6/2013 | Ma .................. G06K 9/00335 382/100 |
| 9,324,145 B1 * | 4/2016 | Cherevatsky ............ G06T 7/42 |

(Continued)

FOREIGN PATENT DOCUMENTS

WO    WO2014036473 A1    3/2014

OTHER PUBLICATIONS

International Search Report dated Feb. 1, 2016 in corresponding International Patent Application No. PCT/US2015/027875.
(Continued)

*Primary Examiner* — Aklilu K Woldemariam (57) ABSTRACT

A method and apparatus for medical image synthesis is disclosed, which synthesizes a target medical image based on a source medical image. The method can be used for synthesizing a high dose computed tomography (CT) image or a high kV CT image from a low dose CT image or a low kV image. A plurality of image patches are extracted from a source medical image. A synthesized target medical image is generated from the source medical image by calculating voxel values in the synthesized target medical image based on the image patches extracted from the source medical image using a machine learning based probabilistic model.

15 Claims, 5 Drawing Sheets

(51) Int. Cl.
*G06T 11/00* (2006.01)
*A61B 6/03* (2006.01)

(52) U.S. Cl.
CPC .. *G06T 11/008* (2013.01); *G06T 2207/10081* (2013.01); *G06T 2207/20081* (2013.01); *G06T 2207/20212* (2013.01); *G06T 2207/30004* (2013.01)

(58) Field of Classification Search
CPC ......... G06T 11/005; G06T 2207/10016; G06T 2207/10068; G06T 2207/10101; G06T 2207/10116; G06T 2207/20092; G06T 2207/30032; G06T 2207/30052; G06T 2207/30068; G06T 2207/30072; G06T 2207/30101; G06T 2207/30168; G06T 2207/30204; G06T 5/50; G06T 7/0008; G06T 7/12; G06T 7/155; G06T 7/42; G06T 7/62; G06T 7/77; G06T 7/80; G06T 2207/10024; G06T 2207/10028; G06T 2207/30196; G06T 2207/30236; G06T 2207/30252; G06T 7/0046; G06T 7/75; G06T 7/11; G06T 2210/41; G06T 2211/40; G06T 11/008; G06T 2207/10081; G06T 2207/20081; G06T 2207/20212; G06T 11/60; G06T 2200/04; G06T 2200/32; G06T 2207/10092; G06T 2207/20021; G06T 2207/30016; G06T 7/0012; G06T 2207/30004; G06T 2207/20076; G06T 7/143; G06T 7/337; G06K 9/66; G06K 2209/051; G06K 2209/053; G06K 9/00127; G06K 9/52; G06K 9/6212; G06K 9/6277; G06K 2009/05; G06K 9/00382; G06K 9/00389; G06K 9/00624; G06K 9/342; G06K 9/6219; G06K 9/6256; G06K 9/6259; G06K 9/627; G06K 9/6282; G06K 2209/15; G06K 9/00335; G06K 9/00785; G06K 9/3233; G06K 9/325; G06K 9/6217; G06K 9/6218; G06K 9/6267; G06K 9/6292; G06K 9/6255; G06K 2209/05; G06K 9/6244; G06K 9/6289; G06K 9/4604; G06K 2009/4666; G06K 9/00208; G06K 9/3241; G06K 9/4671; G06K 9/4676; A61B 19/5244; A61B 1/00009; A61B 1/041; A61B 5/066; A61B 6/461; A61B 6/482; A61B 6/502; A61B 6/5217; A61B 2576/026; A61B 6/03; A61B 6/5235; A61B 5/0035; A61B 5/0042; A61B 5/055; A61B 5/7425; A61B 5/7282; G06F 19/30; G06F 19/00; G01C 11/06; G01N 2035/0418; G01N 2035/0498; G01N 21/952; G01N 35/00732; G05B 21/00; G05B 21/02; G16H 30/40; G16H 50/20; G16H 30/20; H04N 7/18; G01R 33/5608; G01R 33/50; G01R 33/5602
USPC ........ 382/100, 103, 159, 160, 170, 128, 154
See application file for complete search history.

(56) References Cited

U.S. PATENT DOCUMENTS

| | | | | |
|---|---|---|---|---|
| 2009/0303342 | A1* | 12/2009 | Corcoran | G06K 9/00228 348/222.1 |
| 2010/0040285 | A1* | 2/2010 | Csurka | G06K 9/00624 382/170 |
| 2011/0064308 | A1* | 3/2011 | Stein | G06K 9/4638 382/170 |
| 2011/0110581 | A1* | 5/2011 | Yang | G06K 9/00201 382/154 |
| 2011/0157387 | A1* | 6/2011 | Han | H04N 5/2253 348/218.1 |
| 2012/0209514 | A1* | 8/2012 | Chrysanthakopoulos | G06F 16/7837 701/431 |
| 2013/0016889 | A1* | 1/2013 | Myronenko | G06T 7/337 382/131 |
| 2014/0270350 | A1* | 9/2014 | Rodriguez-Serrano | G06K 9/6217 382/103 |
| 2014/0363076 | A1* | 12/2014 | Han | G06K 9/6259 382/159 |
| 2016/0133037 | A1* | 5/2016 | Vemulapalli | G06T 11/60 382/128 |
| 2016/0210749 | A1* | 7/2016 | Nguyen | A61B 5/00 |
| 2016/0314600 | A1* | 10/2016 | Nguyen | G06T 11/003 |
| 2017/0124704 | A1* | 5/2017 | Wu | G01N 21/952 |

OTHER PUBLICATIONS

Cabezas, et al.; "A Review of Atlas-Based Segmentation for Magnetic Resonance Brain Images," Jul. 27, 2011; Computer Methods and Programs in Biomedicine, Elsevier, Amsterdam, NL, vol. 104, No. 3.

Suzuki, et al; Supervised Conversion of Ultra-low-Dose to Higherdose CT Images by Using Pixel-based Machine Learning: Phantom and Initial Patient Studies. Radiological Society of North America 2013.

* cited by examiner

METHOD AND SYSTEM FOR SYNTHESIZING VIRTUAL HIGH DOSE OR HIGH KV COMPUTED TOMOGRAPHY IMAGES FROM LOW DOSE OR LOW KV COMPUTED TOMOGRAPHY IMAGES

BACKGROUND OF THE INVENTION

The present invention relates to synthesize medical image data, and more particularly, to synthesizing virtual high dose or high kV computed tomography images from low dose or low kV computed tomography images.

Computed tomography (CT) combines a series of X-ray images taken from different angles and uses computer processing to create cross-sectional images, or slices, of bones, blood vessels and soft tissues inside the body. The cross-sectional images, or slices, can be combined to reconstruct 3D CT volumes. CT scans can be used to visualize nearly all parts of the body and are used to diagnose disease or injury as well as to plan medical, surgical or radiation treatment. For example, CT scans can be used to diagnose muscle and bone disorders such as bone tumors and fractures, to determine the location of tumors, infections, or blood clots in a patient's body, to guide procedures such as surgery, biopsy, and radiation therapy, to detect and monitor diseases and conditions such as cancer, heart disease, lung nodules, and liver masses, to monitor the effectiveness of disease treatments, and to detect internal injuries and internal bleeding.

During a CT scan a patient is exposed to ionizing radiation. Reducing the dose of radiation to which a patient is exposed in a CT scan is highly desirable. However, high dose CT scans typically produce high quality CT images, and there is a tradeoff between the reducing the radiation dose level of a CT scan and the image quality of the CT images resulting from the scan. Another parameter that affects the quality of CT scans is the tube potential (kV) of the x-ray tube used to acquire the CT images. Low kV CT scans are typically preferred because lower kV values can result in higher attenuation values and image contrast and can also result in a decrease in radiation dose. However, low kV CT scans result in an increase in image noise as compared to high kV CT scans.

BRIEF SUMMARY OF THE INVENTION

The present invention provides a method and system for synthesizing virtual target medical images from source medical images using a probabilistic model and machine learning. Embodiments of the present invention synthesize high dose CT images from low dose CT images or synthesize high kV CT images from low kV images. Embodiments of the present invention can also be applied to other imaging modalities as well to generate a synthesized target medical image from a corresponding source medical image. Embodiments of the present invention can be applied where there is a tradeoff between image quality and some other factor in order to synthesize a virtual high quality image from an acquired lower quality image for which the other factor is improved as compared to the case in which the high quality image is acquired directly.

In one embodiment of the present invention, a plurality of image patches are extracted from a source medical image. A synthesized target medical image is generated from the source medical image by calculating voxel values in the synthesized target medical image based on a probabilistic model that combines a likelihood function that calculates a probability for the voxel values in the synthesized target medical image based on the image patches extracted from the source medical image and a prior function that calculates a probability for the voxel values in the synthesized target medical image based on a predetermined condition associated the synthesized target medical image.

These and other advantages of the invention will be apparent to those of ordinary skill in the art by reference to the following detailed description and the accompanying drawings.

DETAILED DESCRIPTION

The present invention relates to a method and system for synthesizing a virtual target medical image from an acquired source medical image. Embodiments of the present invention are described herein to give a visual understanding of the medical image synthesis method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention provide a framework for synthesizing a target medical image from a source medical image. Embodiments of the present invention can be used in cases in which there is a tradeoff between image quality and some other factor for a particular type of imaging modality, such as radiation dose, acquisition speed, frame rate, transducer frequency, tube potential, field of view, rotation speed, cost, etc., in order to synthesize a virtual high quality medical image from an acquired lower quality medical image for which the other factor is improved as compared to the case in which the high quality image is acquired directly. Embodiments of the present invention may also be used to synthesize a virtual image of one imaging modality from an acquired image of a different imaging modality. Embodiments of the present invention are described herein using the examples of synthesizing a high dose computed tomography (CT) volume from an acquired low dose CT volume and synthesizing a high kV CT volume from a low kV CT volume. However, the present invention is not limited to these examples and can be similarly applied to perform synthesis of any type of virtual target medical image from any type of acquired source medical image.

Figure 1:
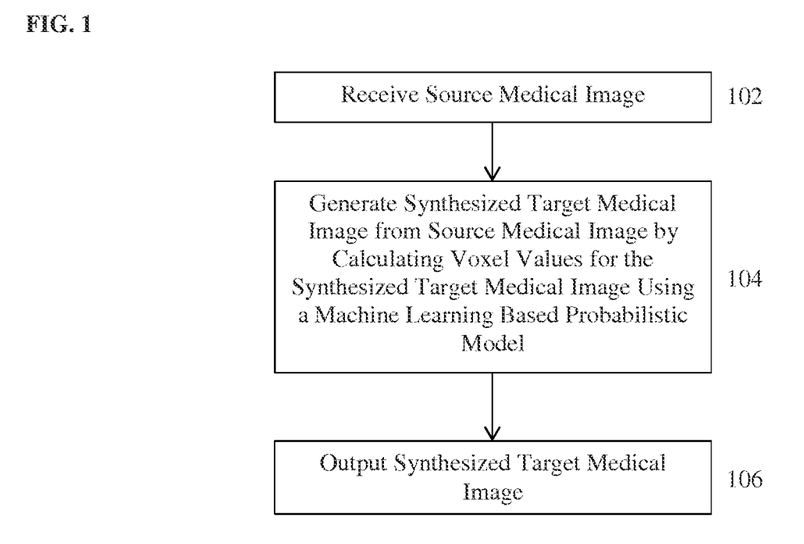
FIG. 1 illustrates a method of synthesizing a virtual target medical image from an acquired source medical image according to an embodiment of the present invention.

FIG. 1 illustrates a method of synthesizing a virtual target medical image from an acquired source medical image according to an embodiment of the present invention. The method of FIG. 1 transforms image data representing a patient's anatomy in the source medical image to generate a new synthesized target medical image volume. The method of FIG. 1 can be used to generate a high dose CT volume from an acquired low dose CT volume or to generate a high kV CT volume for a low kV CT volume, but the present invention is not limited thereto.

At step 102, a source medical image is received. For example, in an advantageous implementation, the source medical image can be a low dose 3D CT volume or a low kV 3D CT volume of an anatomical region of a patient. However, in other possible implementations, the source medical image can be any type of medical image acquired using any medical imaging modality. For example, the source medical image can be any type of "low quality" image, for which acquisition of a corresponding high quality image is possible. Furthermore, the present invention is not limited to 3D medical images and may be similarly applied to 2D medical images as well. Although the methods of FIGS. 1 and 2 can be applied to 2D or 3D medical images, the term "voxel" is used herein to refer to an element of an image regardless of the dimensionality of the image. The source medical image may be received directly from an image acquisition device, such as a CT scanner, or may be received by loading the source medical image from a memory or storage of a computer system or by receiving the source medical image at a computer system via a network transmission from another computer system.

At step 104, a synthesized target medical image is generated by calculating voxel values for the synthesized target medical image using a machine learning based probabilistic model. The synthesized target medical image is a new image of a target image type generated based on the received source medical image. The synthesized target medical image is a virtual image in the sense that it is generated by a computer system performing the methods of FIGS. 1 and 2 based on an the already acquired source medical image, and not acquired using an image acquisition device. The synthesized target medical image can represent a high quality medical image and can be an approximation of a high quality image that could be acquired using a particular type of image acquisition. In an advantageous embodiment, the target medical image can be a synthesized high dose 3D CT volume (generated from an acquired low dose CT volume) or a synthesized high kV 3D CT volume (generated from an acquired low kV volume), but the present invention is not limited thereto.

Each voxel in the received source medical image has a corresponding voxel in the synthesized target medical image. The voxel values of the synthesized target medical image are calculated using a machine learning based probabilistic model. In an advantageous embodiment, following the principle of maximizing the posterior probability, given an unseen source image V (e.g., low dose CT image) with it voxels indexed by n, a synthetic target image W is generated such that:

$$W = \mathrm{argmax}_W \mathrm{Likelihood}(W|V)\mathrm{Prior}(W), \quad (1)$$

where the term Prior(W) is a prior function that quantifies prior knowledge about the target medical image W and Likelihood(W|V) is a likelihood function that calculates a probability for the synthesized target medical image W given the observed source image V.

The prior function Prior(W) calculates a probability for the synthesized target medical image W based on prior knowledge about the target medical image W. That is, the prior function Prior(W) calculates a probability based on predetermined conditions associated with the target type of image (e.g., high dose CT). For example, the prior function Prior(W) can enforce conditions such as a condition that W is spatially smooth, a condition that W is sparse, or a condition that W obeys statistics learned from a training set of target images (e.g., a set of high dose CT images), etc. The prior function Prior(W) evaluates the voxel values of the synthetic target image W and calculates a probability based on how well the voxel values of the synthetic target image W satisfies the prior knowledge condition. In a possible implementation, the prior function Prior(W) enforces a spatial smoothness condition on the synthetic target medical image W by rewarding a synthetic target medical image W with minimized L2-norm. For example, a prior function of $$\mathrm{Prior}(W) = c \; \exp\left(\frac{-\|W\|^2}{\alpha}\right)$$

can be used to enforce the spatial smoothness condition, where c is a normalizing constant and a controls the degrees of smoothness In another possible embodiment, the prior function Prior(W) enforces a sparseness condition on the synthetic target medical image W by rewarding a synthetic target medical image W with minimized L0-norm. For example, a prior function of $$\mathrm{Prior}(W) = c \; \exp\left(\frac{-\|W\|_0}{\alpha}\right)$$

can be used to enforce the sparseness condition. In another possible implementation, statistics can be calculated on a training set of target images and used to implement the prior function Prior(W). For example, the statistics such as mean and standard deviation of the intensity distributions in the training set of target images can be calculated and the prior function Prior(W) can calculate a probability for the intensity distribution of the synthesized target medical image based on a comparison of these statistics in the synthesized target medical image to the statistics calculated for the training set of images. In a possible embodiment, a probability distribution, such as a Gaussian distribution, can be learned from the intensity distributions of the training set of target images and the this probability distribution can be used as Prior(W) to determine a probability for the synthesized target medical image W.

The likelihood function Likelihood(W|V) is modeled from a training set of corresponding source images (e.g., low dose CT images) and target images (e.g., high dose CT images) using machine learning methods. In an advantageous embodiment, instead of modeling the image at a holistic level, modeling is performed at an image patch level. During an offline training stage, pairs of source and target images are acquired. Each pair of images is for the same patient and in correspondence. For example, each pair of images can be a corresponding low dose CT image and high dose CT image for the same patient or a corresponding low kV CT image and high kV CT image for the same patient. For each voxel indexed at m, a pair of corresponding image patches $P_m$ and $Q_m$ of a certain size centered at m are stored, with $P_m$ being a source (e.g., low dose) image patch and $Q_m$ being the corresponding target (e.g. high dose) image patch. After repeating this for all voxels for all training image pairs, we end up with set of corresponding source and target training samples $\{(P_m,Q_m); m=1, 2, \ldots, M\}$, where M is the total number of all of the voxels in all of the training image pairs.

The set of corresponding source and target training samples is then used during the online testing phase to determine individual likelihood functions for the voxels in the synthesized target medical image. According to an advantageous embodiment, the likelihood function Likelihood(W|V) can be calculated based on individual likelihood functions for each of the voxels in the synthesized target medical image W. For example, the Likelihood(W|V) can be calculated as Likelihood(W|V)=$\Sigma_n$ Likelihood($W_n|V_n$), where $V_n$ and $W_n$ are corresponding image patches centered at voxel n in the source medical image and the synthesized target medical image, respectively.

Figure 2:
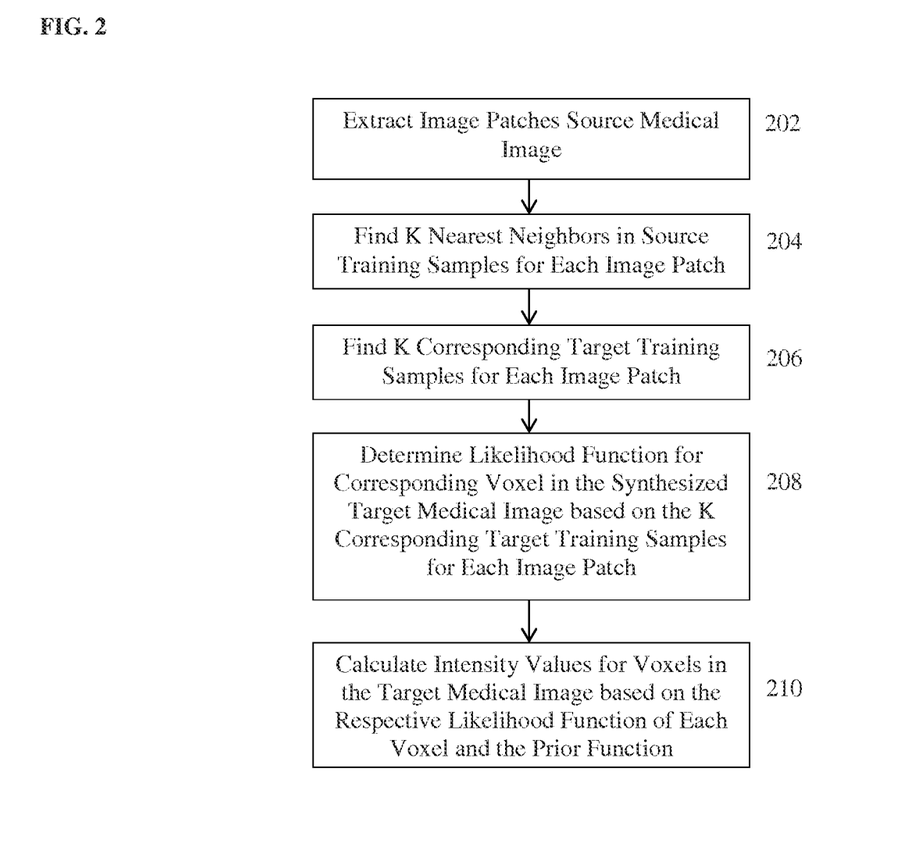
FIG. 2 illustrates a method for calculating voxel values of a synthesized target medical image from a source medical image according to an embodiment of the present invention.

FIG. 2 illustrates a method for calculating voxel values of a synthesized target medical image from a source medical image according to an embodiment of the present invention. The method of FIG. 2 can be used to implement step 104 of FIG. 1. At step 202, a plurality of image patches are acquired from the source medical image. In an advantageous embodiment, a respective image patch centered on each voxel in the source medical image is extracted.

At step 204, K nearest neighbors in the set of source training samples are found for each image patch extracted from the source medical image, That is for each image patch $V_n$ extracted from the source medical image, K nearest neighbor source training samples $\{\overline{P}_k; k=1, 2, \ldots K\}$ are found for the image patch $V_n$ from the set of source training samples $\{P_m; m=1, 2, \ldots M\}$. For example, the K nearest neighbor source training samples are found for an image patch $V_n$ by comparing the image patch $V_n$ to each of the source training samples in the set of source training samples $\{P_m; m=1, 2, \ldots M\}$ using a similarity (or difference) measurement and selecting the K source training samples $\{\overline{P}_k; k=1, 2, \ldots K\}$ that have highest similarity measurement (or lowest difference measurement) with respect the image patch $V_n$. In exemplary implementations, K can be set as K=5-10 (i.e., five to ten nearest neighbors are selected for each image patch), but the present invention is not limited thereto. In a possible implementation, the similarity measure can measure a similarity between the intensity distribution in the image patch $V_n$ and each source training sample image patch. In another possible implementation, a sum of squared distance (SSD) can be used to measure a difference between the intensity distribution in the image patch $V_n$ and each source training sample image patch.

At step 206, K corresponding target training samples are identified for each image patch of the source medical image. The K corresponding target training samples for an image patch $V_n$ are identified based on the K nearest neighbor source training samples $\{\overline{P}_k; k=1, 2, \ldots K\}$ for the image patch $V_n$. In particular, the K corresponding target training samples $\{\overline{Q}_k; k=1, 2, \ldots K\}$ corresponding to the K nearest neighbor source training samples $\{\overline{P}_k; k=1, 2, \ldots K\}$ are identified for each image patch $V_n$.

At step 208, for each image patch in the source medical image, an individual likelihood function for the corresponding voxel in the synthesized target medical image is determined based on the K corresponding target training samples identified for each image patch in the source image. The individual likelihood Likelihood($W_n|V_n$) for each voxel n in the synthesized target medical image can be defined as a function of $(W_n, \overline{Q}_1, \ldots, \overline{Q}_K)$, where $W_n$ is an image patch of the synthesized target medical image centered at voxel n and $\{\overline{Q}_k; k=1, 2, \ldots K\}$ are the K corresponding target training samples identified for the image patch $V_n$ centered at voxel n in the source medical image. In an advantageous embodiment, a probability distribution for each voxel n in the synthesized target medical image, such as a Gaussian distribution or a mixture of Gaussians or other functions, can be learned from the intensity distributions of the K corresponding target training samples $\{\overline{Q}_k; k=1, 2, \ldots K\}$ identified for the corresponding image patch $V_n$ centered at voxel n in the source medical image. This probability function can be used as the individual likelihood function Likelihood($W_n|V_n$) for voxel n in the synthesized target medical image. In this case, the individual likelihood function Likelihood($W_n|V_n$) for each voxel n can calculate a probability for the intensity distribution in the image patch $W_n$ centered at each voxel n using the learned probability distribution.

At step 210, the voxel values of the synthesized target medical image are calculated based on the respective individual likelihood function for each of the voxels in the synthesized target medical image and the prior function for the synthesized target medical image. In particular, voxel intensity values are calculated to maximize the probability function of Equation (1) that combines the likelihood function and the prior function: W=argmax$_W$ Likelihood(W|V) Prior(W), wherein the likelihood function Likelihood(W|V) is calculated from the individual likelihood functions Likelihood($W_n|V_n$) for all of the voxels in the synthesized target medical image. The prior function Prior(W) is calculated as described above. The voxel intensity values that maximize the probability function of Equation (1) can be calculated using any known optimization technique, such as but not limited to gradient descent. This results in the synthesized target medical image.

Returning to FIG. 1, at step 106, the synthesized target medical image is output. For example, the synthesized target medical image can be output by displaying the synthesized target medical image on a display device of a computer system.

The methods of FIGS. 1 and 2 can be used to synthesize a high dose CT image from an acquired low dose CT image. In this case, the synthesis of the high dose CT image provides an image with the high quality of high dose CT imaging while the patient is only exposed to the low dose of radiation associated with acquiring the low dose CT image. The methods of FIGS. 1 and 2 can also be used to synthesize a high kV CT image from an acquired low kV CT image. The synthesis of the high kV CT image provides an image with the high quality and low noise associated with high kV CT imaging and the original low kV CT image provides high attenuation and contrast, with only a low kV CT scan of the patient required. The methods of FIGS. 1 and 2 can be similarly applied to other imaging modalities and imaging domains as well. For example, in Ultrasound, the use of a high frequency in image acquisition results in less noise but the signal cannot penetrate as well, and the use of a low frequency allows for greater signal penetration but more noise. According to an exemplary embodiment of the present invention, a low frequency ultrasound image can be acquired and the methods of FIGS. 1 and 2 can be used to synthesize a virtual high frequency ultrasound image. In this case, the acquired low frequency ultrasound image provides the an image with greater signal penetration and the synthesized high frequency medical image provides an image with a higher image quality and less noise, while only acquisition of the low frequency ultrasound is required. As described above, the methods of FIGS. 1 and 2 can be applied to any case in which there is a tradeoff between image quality and some other factor related to image acquisition, such as radiation dose, acquisition speed, frame rate, transducer frequency, tube potential, field of view, rotation speed, cost, etc., in order to synthesize a virtual high quality medical image from an acquired lower quality medical image for which the other factor related to image acquisition is improved as compared to the case in which the high quality image is acquired directly.

Figure 3:
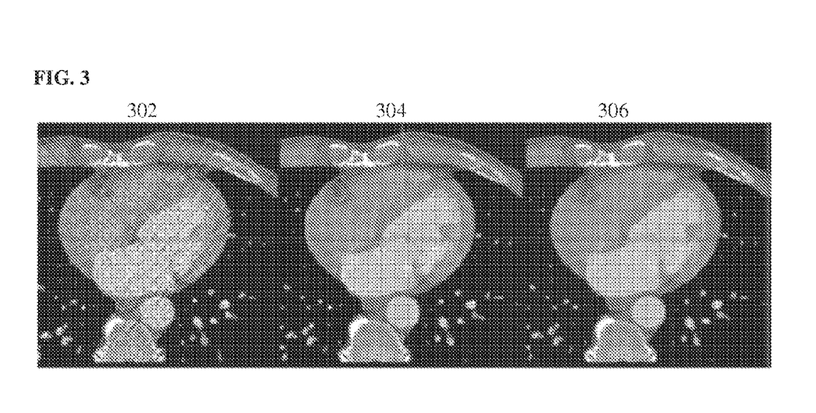
FIG. 3 illustrates exemplary results for synthesizing a high dose CT image from a low dose CT image in a first cardiac CT scan.

FIG. 3 illustrates exemplary results for synthesizing a high dose CT image from a low dose CT image in a first cardiac CT scan. A shown in FIG. 3, image 302 shows a low dose CT image, image 304 shows a ground truth high dose CT that was acquired in a high dose CT scan, and image 306 shows a synthesized high dose CT image generated based on the low dose CT image 302 using the methods of FIGS. 1 and 2.

Figure 4:
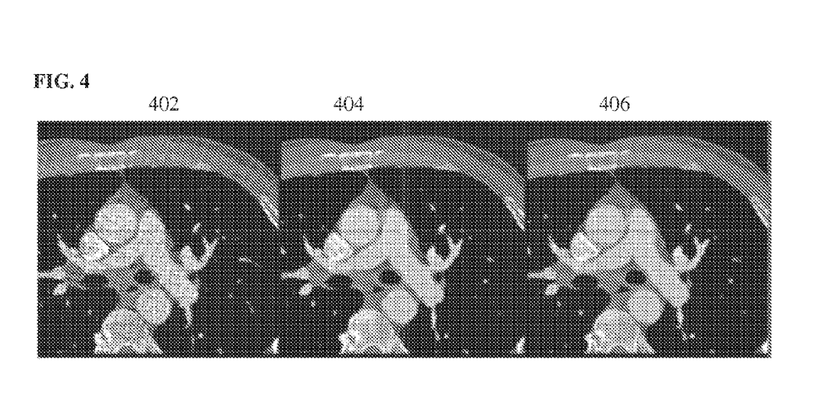
FIG. 4 illustrates exemplary results for synthesizing a high dose CT image from a low dose CT image in a second cardiac CT scan.

FIG. 4 illustrates exemplary results for synthesizing a high dose CT image from a low dose CT image in a second cardiac CT scan. A shown in FIG. 4, image 402 shows a low dose CT image, image 404 shows a ground truth high dose CT that was acquired in a high dose CT scan, and image 406 shows a synthesized high dose CT image generated based on the low dose CT image 402 using the methods of FIGS. 1 and 2.

Figure 5:
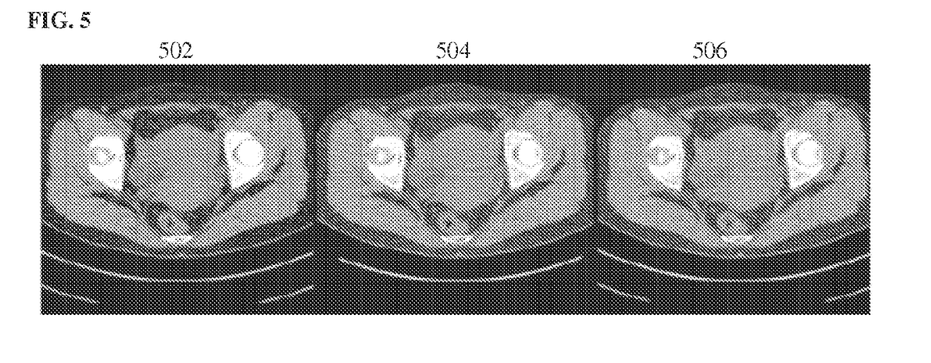
FIG. 5 illustrates exemplary results for synthesizing a high kV CT image from a low kV CT image in an abdominal CT scan.
Figure 6:
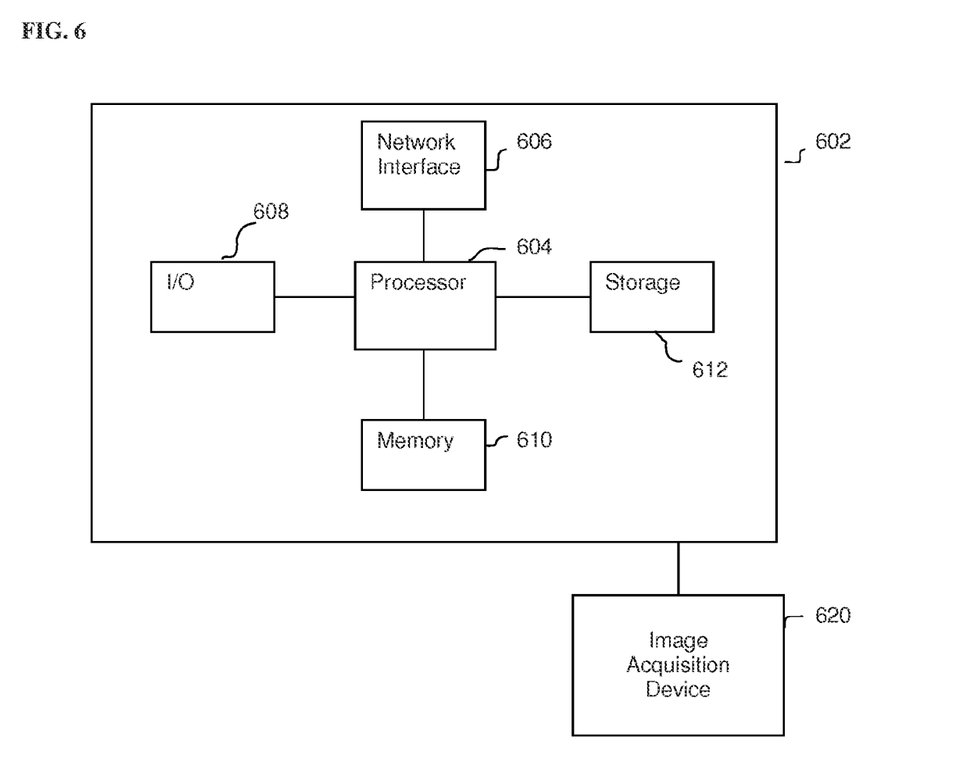
FIG. 6 is a high-level block diagram of a computer capable of implementing the present invention.

FIG. 5 illustrates exemplary results for synthesizing a high kV CT image from a low kV CT image in an abdominal CT scan. A shown in FIG. 5, image 502 shows a low kV CT image, image 504 shows a ground truth high kV CT that was acquired in a high kV CT scan, and image 506 shows a synthesized high kV CT image generated based on the low KV CT image 502 using the methods of FIGS. 1 and 2. The above-described methods for medical image synthesis may be implemented on a computer using well-known computer processors, memory units, storage devices, computer software, and other components. A high-level block diagram of such a computer is illustrated in FIG. 6. Computer 602 contains a processor 604, which controls the overall operation of the computer 602 by executing computer program instructions which define such operation. The computer program instructions may be stored in a storage device 612 (e.g., magnetic disk) and loaded into memory 610 when execution of the computer program instructions is desired. Thus, the steps of the methods of FIGS. 1 and 2 may be defined by the computer program instructions stored in the memory 610 and/or storage 612 and controlled by the processor 604 executing the computer program instructions. An image acquisition device 620, a CT scanning device, can be connected to the computer 602 to input image data to the computer 602. It is possible to implement the image acquisition device 620 and the computer 602 as one device. It is also possible that the image acquisition device 620 and the computer 602 communicate wirelessly through a network. In a possible embodiment, the computer 602 can be located remotely with respect to the image acquisition device 620 and the method steps described herein can be performed as part of a server or cloud based service. The computer 602 also includes one or more network interfaces 606 for communicating with other devices via a network. The computer 602 also includes other input/output devices 608 that enable user interaction with the computer 602 (e.g., display, keyboard, mouse, speakers, buttons, etc.). Such input/output devices 608 may be used in conjunction with a set of computer programs as an annotation tool to annotate volumes received from the image acquisition device 620. One skilled in the art will recognize that an implementation of an actual computer could contain other components as well, and that FIG. 6 is a high level representation of some of the components of such a computer for illustrative purposes.

The above-described methods for medical image synthesis may be implemented using computers operating in a client-server relationship. Typically, in such a system, the client computers are located remotely from the server computer and interact via a network. The client-server relationship may be defined and controlled by computer programs running on the respective client and server computers.

The above-described methods for medical image synthesis may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the method steps described herein, including one or more of the steps of FIGS. 1 and 2. Certain steps of the methods described herein, including one or more of the steps of FIGS. 1 and 2, may be performed by a server or by another processor in a network-based cloud-computing system. Certain steps of the methods described herein, including one or more of the steps of FIGS. 1 and 2, may be performed by a client computer in a network-based cloud computing system. The steps of the methods described herein, including one or more of the steps of FIGS. 1 and 2, may be performed by a server and/or by a client computer in a network-based cloud computing system, in any combination.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for synthesizing a target medical image from a source medical image comprising:
  extracting a plurality of image patches from a source medical image; and
  generating a synthesized target medical image from the source medical image by calculating voxel values in the synthesized target medical image based on a probabilistic model that combines: 1) a likelihood function that calculates a first probability for the voxel values in the synthesized target medical image based on the image patches extracted from the source medical image, and 2) a prior function that calculates a second probability for the voxel values in the synthesized target medical image based on a predetermined condition associated the synthesized target medical image, wherein the prior function comprises at least one of: a probability function learned from intensity distributions in a set of target training samples, a function that calculates the second probability based on a spatial smoothness condition, and a function that calculates the second probability based on a sparseness condition, and wherein generating the synthesized target medical image from the source medical image comprises:

detecting K nearest neighbors in a set of source training samples for each of the plurality of image patches in the source medical image;

identifying K corresponding target training samples from the K nearest neighbors in the set of source training samples for each of the plurality of image patches in the source medical image;

determining an individual likelihood function for each of a plurality of voxels in the synthesized target medical image based on the K corresponding target training samples identified for a respective one of the plurality of image patches of the source medical image centered at a corresponding voxel in the source medical image; and calculating the likelihood function as a sum of probabilities calculated by the individual likelihood function for each of the plurality of voxels in the synthesized target medical image.

2. The method of claim 1, wherein determining an individual likelihood function for each of a plurality of voxels in the synthesized target medical image based on the K corresponding target training samples identified for a respective one of the plurality of image patches of the source medical image centered at a corresponding voxel in the source medical image comprises:

for each of the plurality of voxels in the synthesized target medical image, learning a probability function based on intensity distributions in the K corresponding target training samples identified for the respective one of the plurality of image patches of the source medical image centered at the corresponding voxel in the source medical image.

3. The method of claim 2, wherein learning a probability function based on intensity distributions in the K corresponding target training samples identified for the respective one of the plurality of image patches of the source medical image centered at the corresponding voxel in the source medical image comprises:

learning a Gaussian distribution based on the intensity distributions in the K corresponding target training samples identified for the respective one of the plurality of image patches of the source medical image centered at the corresponding voxel in the source medical image.

4. The method of claim 1, wherein generating a synthesized target medical image from the source medical image comprises:

calculating voxel values for the plurality of voxels in the synthesized target medical image to maximize the probabilistic model.

5. The method of claim 1, wherein the source medical image is a low dose computed tomography (CT) image and the synthesized target medical image is a synthesized high dose CT image.

6. The method of claim 1, wherein the source medical image is a low kV computed tomography (CT) image and the synthesized target medical image is a synthesized high kV CT image.

7. An apparatus for synthesizing a target medical image from a source medical image comprising:

means for extracting a plurality of image patches from a source medical image; and means for generating a synthesized target medical image from the source medical image by calculating voxel values in the synthesized target medical image based on a probabilistic model that combines: 1) a likelihood function that calculates a first probability for the voxel values in the synthesized target medical image based on the image patches extracted from the source medical image, and 2) a prior function that calculates a second probability for the voxel values in the synthesized target medical image based on a predetermined condition associated the synthesized target medical image, wherein the prior function comprises at least one of: a probability function learned from intensity distributions in a set of target training samples, a function that calculates the second probability based on a spatial smoothness condition, and a function that calculates the second probability based on a sparseness condition, and wherein the means for generating the synthesized target medical image from the source medical image comprises:

means for detecting K nearest neighbors in a set of source training samples for each of the plurality of image patches in the source medical image;

means for identifying K corresponding target training samples from the K nearest neighbors in the set of source training samples for each of the plurality of image patches in the source medical image;

means for determining an individual likelihood function for each of a plurality of voxels in the synthesized target medical image based on the K corresponding target training samples identified for a respective one of the plurality of image patches of the source medical image centered at a corresponding voxel in the source medical image; and means for calculating the likelihood function as a sum of probabilities calculated by the individual likelihood function for each of the plurality of voxels in the synthesized target medical image.

8. The apparatus of claim 7, wherein the means for generating a synthesized target medical image from the source medical image comprises:

means for calculating voxel values for the plurality of voxels in the synthesized target medical image to maximize the probabilistic model.

9. The apparatus of claim 7, wherein the source medical image is a low dose computed tomography (CT) image and the synthesized target medical image is a synthesized high dose CT image.

10. The apparatus of claim 7, wherein the source medical image is a low kV computed tomography (CT) image and the synthesized target medical image is a synthesized high kV CT image.

11. A non-transitory computer readable medium storing computer program instructions for synthesizing a target medical image from a source medical image, the computer program instructions when executed by a processor cause the processor to perform operations comprising:

extracting a plurality of image patches from a source medical image; and generating a synthesized target medical image from the source medical image by calculating voxel values in the synthesized target medical image based on a probabilistic model that combines: 1) a likelihood function that calculates a first probability for the voxel values in the synthesized target medical image based on the image patches extracted from the source medical image, and 2) a prior function that calculates a second probability for the voxel values in the synthesized target medical image based on a predetermined condition associated the synthesized target medical image, wherein the prior function comprises at least one of: a probability function learned from intensity distributions in a set of target training samples, a function that calculates the second probability based on a spatial smoothness condition, and a function that calculates the second probability based on a sparseness condition, and wherein generating the synthesized target medical image from the source medical image comprises:

detecting K nearest neighbors in a set of source training samples for each of the plurality of image patches in the source medical image;

identifying K corresponding target training samples from the K nearest neighbors in the set of source training samples for each of the plurality of image patches in the source medical image;

determining an individual likelihood function for each of a plurality of voxels in the synthesized target medical image based on the K corresponding target training samples identified for a respective one of the plurality of image patches of the source medical image centered at a corresponding voxel in the source medical image; and calculating the likelihood function as a sum of probabilities calculated by the individual likelihood function for each of the plurality of voxels in the synthesized target medical image.

12. The non-transitory computer readable medium of claim 11, wherein determining an individual likelihood function for each of a plurality of voxels in the synthesized target medical image based on the K corresponding target training samples identified for a respective one of the plurality of image patches of the source medical image centered at a corresponding voxel in the source medical image comprises:

for each of the plurality of voxels in the synthesized target medical image, learning a probability function based on intensity distributions in the K corresponding target training samples identified for the respective one of the plurality of image patches of the source medical image centered at the corresponding voxel in the source medical image.

13. The non-transitory computer readable medium of claim 11, wherein generating a synthesized target medical image from the source medical image comprises:

calculating voxel values for the plurality of voxels in the synthesized target medical image to maximize the probabilistic model.

14. The non-transitory computer readable medium of claim 11, wherein the source medical image is a low dose computed tomography (CT) image and the synthesized target medical image is a synthesized high dose CT image.

15. The non-transitory computer readable medium of claim 11, wherein the source medical image is a low kV computed tomography (CT) image and the synthesized target medical image is a synthesized high kV CT image.

* * * * *